(12) United States Patent
Yoshida et al.

(10) Patent No.: US 9,224,574 B2
(45) Date of Patent: Dec. 29, 2015

(54) CHARGED PARTICLE OPTICAL EQUIPMENT AND METHOD FOR MEASURING LENS ABERRATION

(75) Inventors: Takaho Yoshida, Higashimurayama (JP); Hisanao Akima, Sendai (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 13/883,034

(22) PCT Filed: Nov. 4, 2011

(86) PCT No.: PCT/JP2011/075517
§ 371 (c)(1),
(2), (4) Date: Jun. 4, 2013

(87) PCT Pub. No.: WO2012/063749
PCT Pub. Date: May 18, 2012

(65) Prior Publication Data
US 2013/0256531 A1    Oct. 3, 2013

(30) Foreign Application Priority Data

Nov. 12, 2010  (JP) .................................. 2010-253477

(51) Int. Cl.
| H01J 37/153 | (2006.01) |
| H01J 37/244 | (2006.01) |
| H01J 37/28 | (2006.01) |
| G01N 23/00 | (2006.01) |

(52) U.S. Cl.
CPC ............. *H01J 37/153* (2013.01); *H01J 37/244* (2013.01); *H01J 37/28* (2013.01); *G01N 23/00* (2013.01)

(58) Field of Classification Search
None
See application file for complete search history.

(56) References Cited

U.S. PATENT DOCUMENTS

| 5,084,622 | A | 1/1992 | Rose | |
| 6,552,340 | B1 * | 4/2003 | Krivanek et al. | 850/7 |
| 7,619,220 | B2 * | 11/2009 | Sawada et al. | 250/311 |
| 7,763,862 | B2 * | 7/2010 | Hosokawa | 250/396 R |
| 8,129,680 | B2 * | 3/2012 | Hirose et al. | 250/307 |
| 8,772,732 | B2 * | 7/2014 | Nakano et al. | 250/396 R |
| 2004/0036030 | A1 * | 2/2004 | Matsuya et al. | 250/396 R |
| 2004/0119022 | A1 | 6/2004 | Sato et al. | |
| 2006/0033037 | A1 * | 2/2006 | Kawasaki et al. | 250/398 |
| 2007/0120055 | A1 * | 5/2007 | Sawada et al. | 250/307 |
| 2007/0158568 | A1 * | 7/2007 | Nakamura et al. | 250/311 |
| 2008/0018460 | A1 * | 1/2008 | Ishiguro et al. | 340/540 |
| 2008/0042074 | A1 * | 2/2008 | Sato et al. | 250/396 R |
| 2009/0212228 | A1 * | 8/2009 | Hirose et al. | 250/396 R |

FOREIGN PATENT DOCUMENTS

| JP | 3207196 B2 | 9/2001 |
| JP | 2004-127930 A | 4/2004 |

(Continued)

*Primary Examiner* — Andrew Smyth
(74) *Attorney, Agent, or Firm* — Mattingly & Malur, PC

(57) ABSTRACT

Beam scanning for obtaining a scanned image is performed by an aberration corrector, which is an aberration measured lens, and a scanning coil disposed above an objective lens, instead of a scanning coil ordinarily placed on the objective lens. Thus, distortion with an aberration of an aberration measured lens is scanned on the surface of a sample, and then a scanned image is formed from a scattered electron beam, a transmission electron beam, or a reflected/secondary electron beam that is generated by the scan, achieving a scanning aberration information pattern equivalent to a conventional Ronchigram. Such means is a feature of the present invention.

9 Claims, 12 Drawing Sheets

(56) References Cited

FOREIGN PATENT DOCUMENTS

| | | | |
|---|---|---|---|
| JP | 2004127930 A * | 4/2004 | |
| JP | 2005-108470 A | 4/2005 | |
| JP | 2005108470 A * | 4/2005 | |
| JP | 2007-180013 A | 7/2007 | |
| JP | 2008-091125 A | 4/2008 | |
| JP | 4204902 B2 * | 1/2009 | |
| JP | 2010-092625 A | 4/2010 | |
| JP | 2010092625 A * | 4/2010 | |

* cited by examiner

F I G . 2
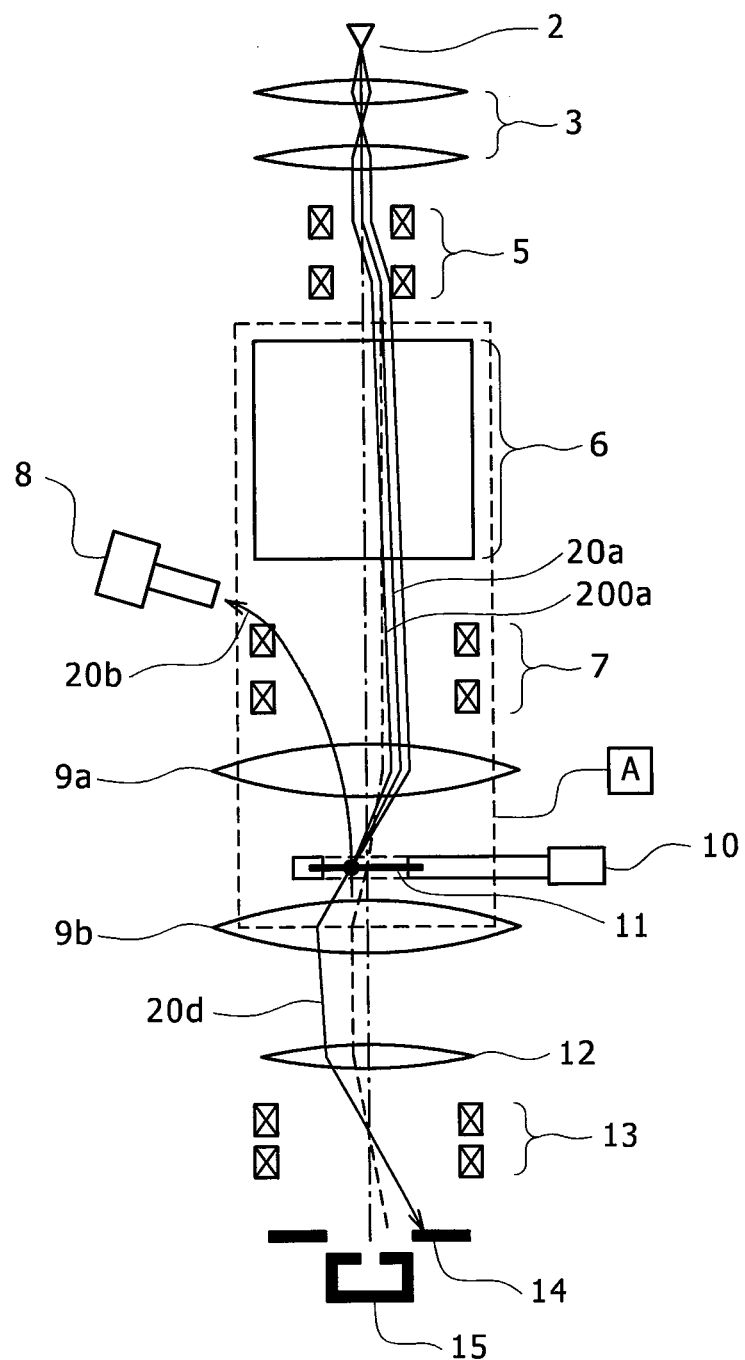

F I G . 6
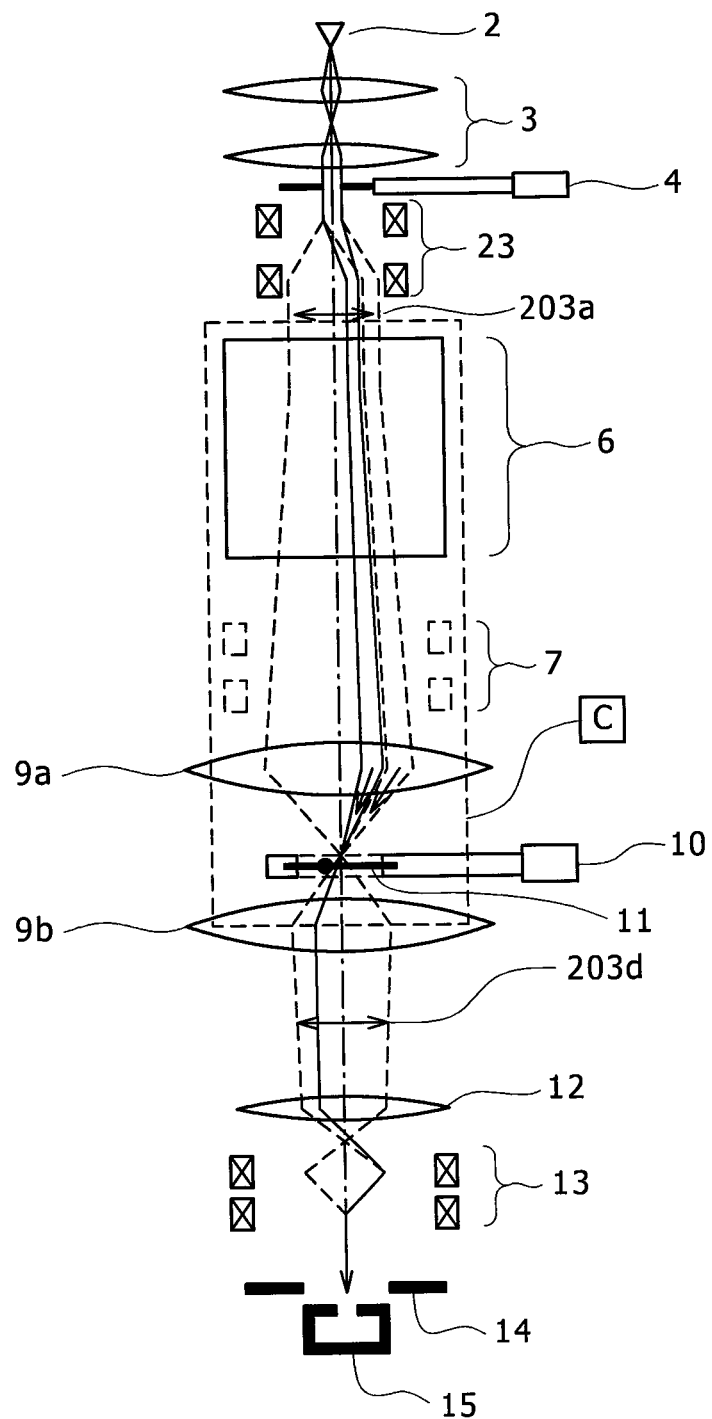

ABERRATION MEASUREMENT/ADJUSTMENT FLOW USING SCANNING RONCHIGRAM — 500

CHARGED PARTICLE OPTICAL EQUIPMENT AND METHOD FOR MEASURING LENS ABERRATION

TECHNICAL FIELD

The present invention relates to a charged particle optical device and a method for measuring a lens aberration, and particularly relates to a method for acquiring aberration information in the method for measuring a lens aberration of the charged particle optical device.

BACKGROUND ART

A scanning electron microscope (SEM) and a scanning transmission electron microscope (STEM) are combined with an electron optical device such as an electron lens to form an extremely small electron beam crossover (hereinafter, will be referred to as a beam probe) on the plane of an observed sample. Transmission scattered electrons, reflected electrons, secondary electrons, or derived X-rays from a small region irradiated by the beam probe are measured to obtain information on the structure and composition of the small region. Furthermore, the electron microscope two-dimensionally scans the beam probe on the plane of a sample by means of an electromagnetic electron beam deflector, obtaining a two-dimensional image (a so-called electron microscope image).

In recent electron microscopes, an advanced technique of aberration correction allows the provision of aberration correctors for compensating the aberrations of an objective lens, e.g., a spherical aberration and a chromatic aberration. Thus, an extremely small beam probe can accurately form an image on the plane of the sample (e.g., see Patent Literatures 1 and 2).

Specifically, the resolutions of electron microscopes have improved. For example, in recent years, a commercially available STEM device having a spherical aberration corrector can obtain a resolution of 0.1 nm or less that is smaller than a typical atomic size by the aberration correcting effect of the aberration corrector. Conversely, there has been an increasing demand for a measuring method for accurately evaluating the aberration state of an electron microscope including an aberration corrector. Thus, some accurate aberration measuring methods have been developed and utilized in parallel with the development of aberration correctors.

Conventionally known aberration measuring methods include an aberration measurement using displacement due to aberrations and a probe tableau method. Another aberration measuring method is an aberration measuring method using a Ronchigram (Ronchigram method).

The aberration measurement using displacement due to aberrations and the probe tableau method require repeated measurements for reducing errors. Thus, it is necessary to expend much time and effort to obtain a set of aberration coefficients.

In the aberration measuring method using a Ronchigram, an aberration can be fundamentally measured from a Ronchigram obtained by a measurement. For example, Patent Literature 3 describes, as an example of the aberration measuring method using a Ronchigram, a method of obtaining a Ronchigram using an amorphous thin-film sample, and then obtaining an autocorrelation in the local region of the Ronchigram, achieving a local strain tensor of the Ronchigram.

Ronchigram is a projected image and thus a measured image can be obtained in a shorter time than a scanned image in the foregoing two methods.

Therefore, an aberration can be measured at a high speed by using a Ronchigram. This method is quite promising in the adjustment of an aberration corrector requiring repeated aberration measurements.

CITATION LIST

Patent Literatures

Patent Literature 1: Japanese Patent No. 3207196
Patent Literature 2: Japanese Patent No. 4204902
Patent Literature 3: Japanese Patent No. 2007-180013

SUMMARY OF INVENTION

Technical Problem

As has been discussed, conventional aberration measuring methods such as an aberration measurement using displacement due to aberrations and a probe tableau method require repeated measurements (acquisition of scanning microscope images) while changing an electron illumination angle, resulting in the need for much time and effort. The conventional methods are particularly disadvantageous in the complicated steps of adjusting an aberration corrector for making an adjustment while measuring an aberration several times, and an extended time for adjustments.

In contrast, in a measuring method using a Ronchigram, an aberration can be measured from a small number of Ronchigrams that can be captured at high speeds. Thus, an aberration is expected to be simply measured in a shorter time. However, as described above, a projected image called a Ronchigram is necessary and thus the method can be used in an SEM. Also in a STEM, a camera is necessary for capturing a Ronchigram.

The present invention provides an aberration measuring method that is applicable to an SEM using a reflected/secondary electron scanning image with the simplicity of a Ronchigram method, and does not particularly need a detector for imaging, or provides a method of acquiring aberration information for an aberration measurement.

Solutions to Problem

A representative configuration of the present invention will be described below.

A method for measuring a lens aberration according to the present invention is a method for measuring lens aberration in a charged particle optical device including means that focuses an electron beam for two-dimensional scanning on a sample, the charged particle optical device including: an electron source that emits an electron beam; sample mounting means for mounting the sample; electromagnetic lenses disposed between the electron source and the sample mounting part; electron beam scanning means that is provided on the electron-optical upstream side of aberration measured lenses of the electromagnetic lenses, and scans and deflect the electron beam; beam diaphragm means that is provided upstream of the electron beam scanning means and focuses the electron beam to a predetermined beam diameter; detecting means that detects an electron signal induced from the sample by the electron beam impinging onto the sample; and control means that controls the electron source, the electromagnetic lenses, the electron beam scanning means, and the detecting means, wherein the electron beam scanning means upstream of the measured lenses scans the electron beam from the electron source so as to two-dimensionally scan a beam probe on the surface of the sample, the beam probe being formed by the electromagnetic lenses, the detecting means detects at least one of signals including a secondary electron, a reflected electron, a transmitted electron, and a scattered electron that are induced by the beam probe projected with a distortion on the surface of the sample according to the aberration of the measured lens, and the control means calculates the aberration amount of the measured lens based on a two-dimensional image obtained in synchronization with scanning on the measured lens.

A charged particle optical device according to the present invention includes: an electron source that emits an electron beam; sample mounting means for mounting a sample; electromagnetic lenses disposed between the electron source and the sample mounting part; electron beam scanning means that is provided on the electron-optical upstream side of aberration measured lenses of the electromagnetic lenses, and scans and deflect the electron beam; and control means that controls the electron source, the electromagnetic lenses, and the electron beam scanning means, wherein the electron beam scanning means upstream of the measured lenses scans the electron beam from the electron source so as to two-dimensionally scan a beam probe on the surface of the sample, the beam probe being formed by the electromagnetic lenses, and the charged particle optical device further includes: detecting means that detects at least one of signals including a secondary electron, a reflected electron, a transmitted electron, and a scattered electron that are induced by the beam probe projected with a distortion on the surface of the sample according to the aberration of the measured lens; and measuring means that measures the aberration amount of the measured lens based on a two-dimensional image obtained in synchronization with scanning on the measured lens.

In other words, beam scanning for obtaining a scanned image is performed by an aberration corrector, which is an aberration measured lens, and a scanning coil disposed above the objective lens, instead of a scanning coil ordinarily placed on the objective lens. Thus, distortion with an aberration of the aberration measured lens is scanned on the surface of a sample, and then a scanned image is formed from a scattered electron beam, a transmission electron beam, or a reflected/secondary electron beam that is generated by the scan, achieving a scanning aberration information pattern equivalent to a conventional Ronchigram. Such means is a feature of the present invention.

Advantageous Effect of Invention

The present invention can provide an aberration measuring method that is also applicable to a SEM using a reflected/secondary electron scanning image with simplicity of a Ronchigram method and does not particularly require a detector for imaging, or a method for acquiring aberration information for aberration measurement.

BRIEF DESCRIPTION OF THE DRAWINGS

FIG. 2 shows an example of a conventional aberration measuring method (an aberration measurement using displacement due to aberrations and a probe tableau method).

FIG. 6 shows an electronic optical setting of a scanning transmission electron microscope, the setting being made for performing a scanning Ronchigram method according to the present invention in the scanning transmission electron microscope.

BEST MODE FOR CARRYING OUT THE INVENTION

An embodiment according to the present invention will be described below with reference to the accompanying drawings.

The present invention is applicable to typical charged particle devices using converging charged particle probes, for example, a scanning electron microscope, a focused ion beam system, and an electron beam lithography system. In the following explanation, the application of the present invention to a scanning electron microscope and a scanning transmission electron microscope will be mainly described in order to clarify problems without using redundant words.

Figure 1:
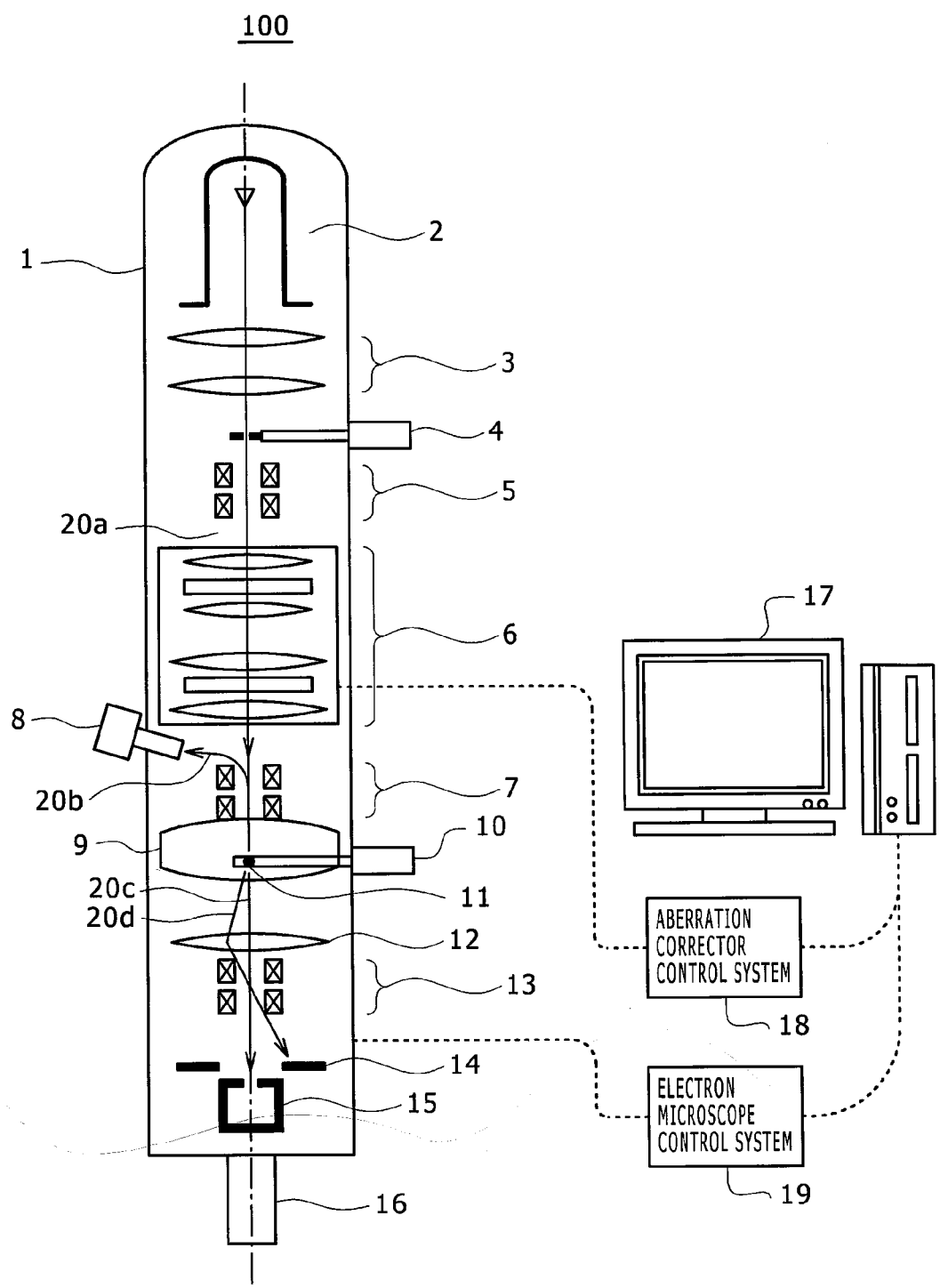
FIG. 1 shows the configuration of a scanning transmission electron microscope including a spherical aberration corrector.

FIG. 1 shows a conventional scanning transmission electron microscope (STEM) 100. In the STEM 100, a transmission scanning electron microscope body 1 contains an electron source 2, converging lenses 3, converging lens diaphragms 4, an electron beam deflector 5, an objective lens 9, and a sample 11. An electron beam from the electron source 2 is accelerated through an accelerating tube, the converging parallel of the beam is adjusted through the converging lenses 3, an electron beam with a proper angular range is selected by the converging lens diaphragm 4, the position and inclination of the beam are adjusted by the electron beam deflector 5, and then the beam is focused so as to form an extremely small beam probe on a surface of the sample 11 through the objective lens 9. The beam probe is scanned on the surface of the sample by a scanning coil 7, allowing a SEM secondary electron/reflected electron detector 8 or a STEM dark field detector 14 and a STEM bright field detector 15 to detect generated secondary electrons and reflected electrons. Furthermore, signals are arranged in response to scanning of the beam probe on the surface of the sample, obtaining two-dimensional information on a sample small region, that is, electron microscope images for the respective signals. An imaging lens 12 and an electron beam deflector 13 are used for adjusting proper detection conditions in the STEM detectors 14 and 15. Obtained electron microscope images are displayed on a control terminal 17 through an electron microscope control system 19 and are observed by a scanning person.

Before an aberration measuring method or an aberration information acquisition method is described according to the related art and the present invention, general matters about the aberrations of electron microscopes will be described below. The aberration of a lens is caused by the imperfection of the lens and is expressed by a displacement of an electron orbit an excessive phase change through an ideal lens (not abbreviated). For example, a phase shift caused by an aberration on the exit surface of the objective lens 9 is expressed as a shift from an ideal wave surface of an electron beam, that is, a wave aberration $\chi(\omega, \omega^c)$ by an expression below. A bar on $\omega$ in (Equation 1) indicates the complex conjugate of $\omega$ and is expressed as $\omega^c$ in the following explanation. The bar on $\omega$ is similarly expressed also in the subsequent expressions.

[Expression 1]

$$X(\omega, \overline{\omega}) = \sum_{n,m} A_{n,m} \omega^n \overline{\omega}^m \quad \text{(Equation 1)}$$

$$= \begin{cases} \frac{1}{2}C_1\omega\overline{\omega} + \frac{1}{2}A_1\overline{\omega}^2 + B_2\omega\overline{\omega}^2 + \frac{1}{3}A_2\overline{\omega}^3 + \\ \frac{1}{4}C_3\omega^2\overline{\omega}^2 + S_3\omega\overline{\omega}^3 + \frac{1}{4}A_3\overline{\omega}^4 + B_4\omega\overline{\omega}^4 + \\ D_4\omega^2\overline{\omega}^4 + \frac{1}{5}A_4\overline{\omega}^5 + \frac{1}{6}C_5\omega^3\overline{\omega}^3 + \\ S_5\omega^2\overline{\omega}^4 + R_5\omega\overline{\omega}^5 + \frac{1}{6}A_5\overline{\omega}^6 \ldots \end{cases}$$

[Expression 2]

$$\chi(\omega, \omega^c) = \chi(\omega, \overline{\omega}) \quad \text{(Equation 1a)}$$

[Expression 3]

$$\chi(\omega, \overline{\omega}) = \text{Re}\{X(\omega, \overline{\omega})\} \quad \text{(Equation 2)}$$

In (Equation 2), Re represents the acquisition of the real part of the equation and the bar on $\omega$ indicates the acquisition of a complex conjugate. $\omega$ is the complex notation of an electron beam entrance angle on the plane of a sample ((x, y) indicates coordinates on the exit surface of the objective lens, and $f_0$ indicates the focal length of the objective lens).

[Expression 4]

$$\omega = \frac{x + iy}{f_o} \quad \text{(Equation 3)}$$

The first line in (Equation 1) indicates an exponential polynomial expansion of $\omega$, $\omega^c$ by a general aberration coefficient $A_{n,m}$ and the second line has a conventional aberration coefficient and an expression that is a quintic expression categorized by an aberration order (n+m) and symmetry (m−n). For example, $C_1$ is defocus, $A_1$ is two-fold symmetry astigmatism, $B_2$ is coma, $A_2$ is three-fold symmetry astigmatism, and $C_3$ is a spherical aberration coefficient.

An aberration measurement is merely a method for measuring these aberration coefficients to determine the original $\chi(\omega, \omega^c)$.

Figure 3:
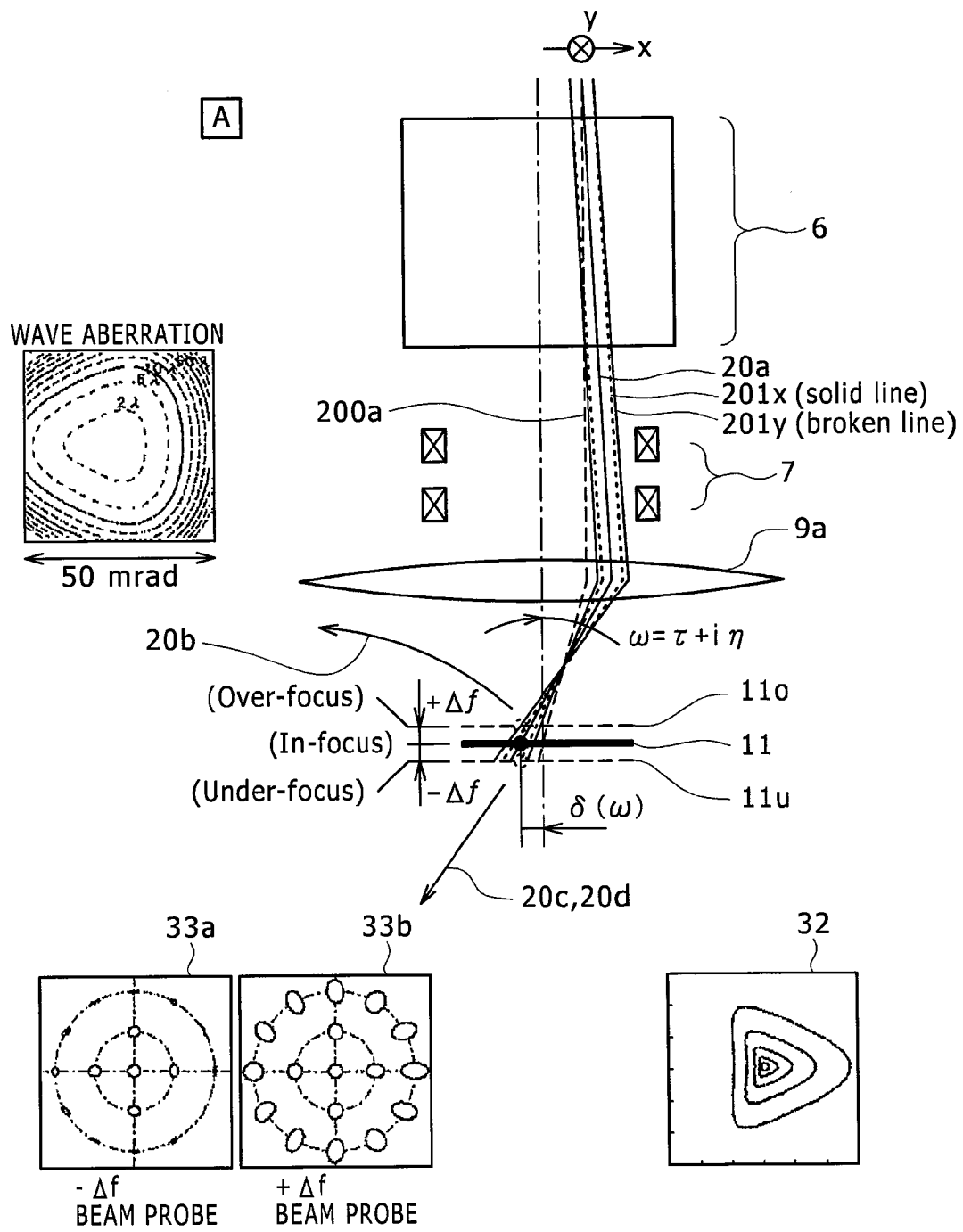
FIG. 3 shows the measurement principles of the conventional aberration measurement using displacement due to aberrations and the conventional probe tableau method according to the related art.

FIG. 2 shows the outline of an electronic optical setting in the STEM for two measuring methods of conventional aberration measuring methods, an aberration measurement using displacement due to aberrations, and a probe tableau method. FIG. 3 is an enlarged view showing A of FIG. 2A to indicate the principles of the methods. First, an aberration in (Equation 1) causes a beam displacement $\delta(\omega)$ on the surface of the sample.

[Expression 5]

$$\delta(\omega) = 2\frac{\partial X(\omega, \overline{\omega})}{\partial \overline{\omega}} \quad \text{(Equation 4)}$$

$$= \begin{cases} C_1\omega + 2A_1\overline{\omega} + 2B_2\omega\overline{\omega} + 2A_2\overline{\omega}^2 + \\ C_3\omega^2\overline{\omega} + 6S_3\omega\overline{\omega}^2 + 2A_3\overline{\omega}^3 + 8B_4\omega\overline{\omega}^3 + \\ 8D_4\omega^2\overline{\omega}^3 + 2A_4\overline{\omega}^4 + C_5\omega^3\overline{\omega}^2 + 8S_5\omega^2\overline{\omega}^3 + \\ 10R_5\omega\overline{\omega}^4 + 2A_5\overline{\omega}^5 \ldots \end{cases}$$

$c_1(\omega)$ is local defocus at $\omega$ and astigmatism $A_1(\omega) \equiv A_{1r}(\omega) + iA_{1i}(w)$ is obtained.

[Expression 6]

$$\begin{aligned} C_1(\tau, \eta) &= C_1 + 4B_{2r}\tau + 4B_{2i}\eta + 2C_3(\eta^2 + \tau^2) - \\ &\quad 6S_3(\eta^2 - \tau^2) - 8B_{4r}\tau(3\eta^2 - \tau^2) - 8B_{4i}\tau(\eta^2 - 3\tau^2) + \\ &\quad 3C_5(\eta^2 + \tau^2)^2 - 16S_{5r}(\eta^4 - \tau^4) - 16S_{5i}(\eta^4 - \tau^4) + \\ &\quad 10R_{5r}(\eta^4 - 6\eta^2\tau^2 + \tau^4) - 40R_{5i}\eta\tau(\eta^2 - \tau^2) \end{aligned} \quad \text{(Equation 5a)}$$

[Expression 7]

$$\begin{aligned} A_{1r}(\tau, \eta) &= A_{1r} + 2B_{2r}\tau - 2B_{2i}\eta - \\ &\quad C_3(\eta^2 - \tau^2) + 6S_{3r}(\eta^2 + \tau^2) - 3A_{3r}(\eta^2 - \tau^2) + \\ &\quad 6A_{3i}\eta\tau + 12B_{4r}\tau(\eta^2 + \tau^2) + 12B_{4i}\eta(\eta^2 + \tau^2) - \\ &\quad 4A_{4r}\tau(3\eta^2 - \tau^2) - 4A_{4i}\eta(\eta^2 - 3\tau^2) - 2C_5(\eta^4 - \tau^4) + \\ &\quad 2S_{5r}(7\eta^4 + 6\eta^2\tau^2 + 7\tau^4) + 2S_{5i}(7\eta^4 + 6\eta^2\tau^2 + 7\tau^4) - \\ &\quad 20R_{5r}(\eta^4 - \tau^4) + 40R_{5i}\eta\tau(\eta^2 + \tau^2) + \\ &\quad 5A_{5r}(\eta^4 - 6\eta^2\tau^2 + \tau^4) - 20A_{5i}\eta\tau(\eta^2 - \tau^2) \end{aligned} \quad \text{(Equation 5b)}$$

[Expression 8]

$$\begin{aligned} A_{1i}(\tau, \eta) &= A_{1i} + 2B_{2r}\eta - 2B_{2i}\tau - 2C_3\eta\tau + \\ &\quad 6S_{3i}(\eta^2 + \tau^2) - 6A_{3r}\eta\tau + 3A_{3i}(\eta^2 - \tau^2) - \\ &\quad 12B_{4r}\eta(\eta^2 + \tau^2) + 12B_{4i}\tau(\eta^2 + \tau^2) - 4A_{4r}\eta(\eta^2 - 3\tau^2) - \\ &\quad 4A_{4r}\tau(3\eta^2 - \tau^2) - 4C_5\eta\tau(\eta^2 + \tau^2) - 8S_{5r}\eta\tau(\eta^2 - \tau^2) - \\ &\quad 8S_{5i}\eta\tau(\eta^2 - \tau^2) - 40R_{5r}\eta\tau(\eta^4 + \tau^4) - 20R_{5i}(\eta^4 - \tau^4) + \\ &\quad 20A_{5r}\eta\tau(\eta^2 - \tau^2) + 5A_{5i}(\eta^4 - 6\eta^2\tau^2 + \tau^4) \end{aligned} \quad \text{(Equation 5c)}$$

(Subscripts r and i in $\omega \equiv \tau + i\eta$ or in the aberration coefficients indicate the real part and the imaginary part of the coefficients. Rotationally symmetric aberrations $C_1$, $C_3$, and $C_5$ having no imaginary parts are not indicated by the subscripts). These amounts represent the defocus of the beam probe, that is, a reduction in resolution. Conversely, aberrations can be measured by measuring these amounts. In order to specifically measure these amounts, as shown in FIG. 2, the position of incidence of the beam is shifted by the deflector 5 relative to an optical system having an aberration to be measured (in FIG. 2, an aberration corrector 6 and a front field 9a of the objective lens that contributes to image formation). Furthermore, the amounts are measured by obtaining a scanning microscope image or a scanning transmission electron microscope image by means of the scanning coil 7. The objective lens includes the front field 9a and a rear field 9b. The aberration corrector 6 is controlled by an aberration corrector control system and a power supply 18 in FIG. 1.

In this case, $\delta(\omega)$ is measured as an image shift while $C_1(\omega_i)$ and $A_1(\omega_i)$ are measured as the defocus and astigmatism of an image. However, as expressed in (Equation 4) and (Equations 5a and 5b), a large number of aberration coefficients to be measured (in consideration of the imaginary parts and the real parts of the coefficients, 25 aberration coefficients up to quintics) need to be determined. Thus, various measurements are made on $\omega_i=\omega$ (i=1, 2, 3, . . . ) satisfying the aberration coefficients, and the aberration coefficients are determined as simultaneous equations in (Equation 4) or (Equations 5a and 5b).

For $\delta(\omega_i)$, an image displacement is plotted with $r_i$ and $\theta_i$ in $\omega \equiv \omega i = r_i e^{2\pi i \theta i}$ and in to obtain a so-called "aberration pattern" 32 in FIG. 3. Hence, the pattern is substantially measured to produce a simultaneous equation for (Equation 4), deriving the aberrations coefficients.

A wave aberration on the upper left of FIG. 3 shows contour lines indicating phase shifts of electronic wave surfaces. $\lambda$ in FIG. 3 indicates an electronic beam wavelength.

For $C_1(\omega_i)$ and $A_1(\omega_i)$, over-focus and under-focus electron microscope images are obtained (11o and 11u in FIG. 3) with an incident angle of $\omega_i \equiv \omega_i$. In a known method, deconvolutions are obtained with reference to $\omega=0$ and in-focus electron microscope images to estimate over-focus and under-focus probe patterns at $\omega \equiv \omega_i$, producing so-called "probe tableaus" 33a and 33b. Furthermore, $C_1(\omega_i)$ and $A_1(\omega_i)$ are measured according to the probe tableaus to form the simultaneous equations of (Equations 5a and 5b). These equations are solved to determine the aberration coefficients.

In FIG. 3, reference numeral 32 indicates an example of an aberration pattern measurement, which can be used for determining a displacement from an in-focus (or proper defocus) microscope image at incidence $\omega$ in when $\omega=0$ is obtained (incidence on the axis), as a change relative to $\omega$.

In FIG. 3, reference numerals 33a and 33b denote examples of the probe tableaus. Proper over-focus (+$\Delta$f) and under-focus (−$\Delta$f) beam probe patterns are estimated with reference to in-focus microscope images incident on the axis. This can determine focus ($C_{1r}$) and two-fold symmetry astigmatism ($A_{1r}$) for $\omega$. In FIG. 3, 33a indicates a −$\Delta$f beam probe, and 33b indicates a +$\Delta$f beam probe.

These methods are advantageous in that an electron microscope image used for measurement is obtained from any one of a reflected secondary electron beam (or secondary electron beam) 20b, a transmitted electron beam 20c, and a scattered electron beam 20d. Thus, these measuring methods can be used for a SEM and a STEM.

These methods are however disadvantageous in that a sufficient number of aberration coefficients are necessary for (Equation 4) and (Equations 5a and 5b) or measurements need to be accordingly repeated to actually reduce an error, requiring much time and effort to obtain a set of aberration coefficients. For example, in order to determine 12 tertiary aberration coefficients in a STEM aberration corrector of CEOS, proper under-focus and over-focus STEM images need to be obtained at 18 electron illumination angles, which is particularly disadvantageous in current adjustments on aberration correctors that correct aberrations while repeatedly measuring and adjusting aberrations.

Figure 4:
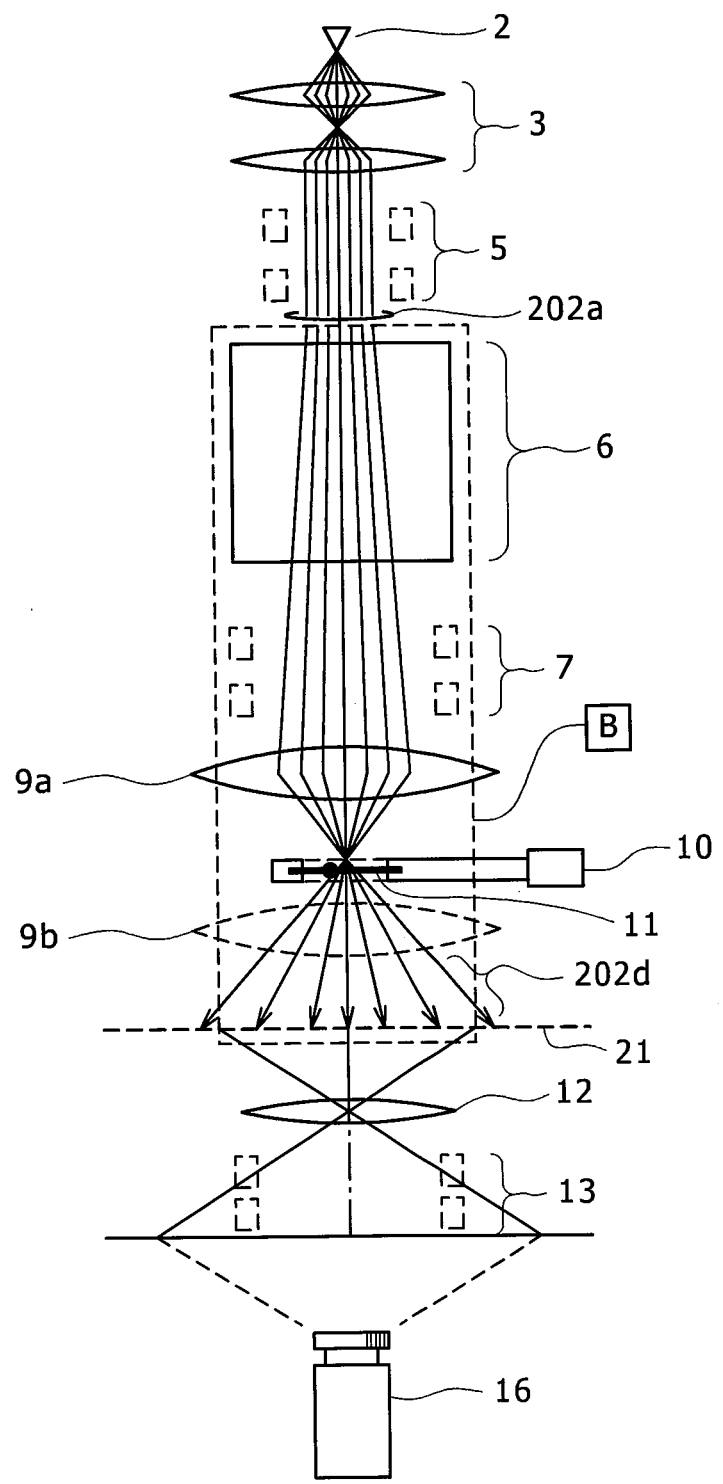
FIG. 4 shows an example of the conventional aberration measuring method (Ronchigram method).
Figure 5:
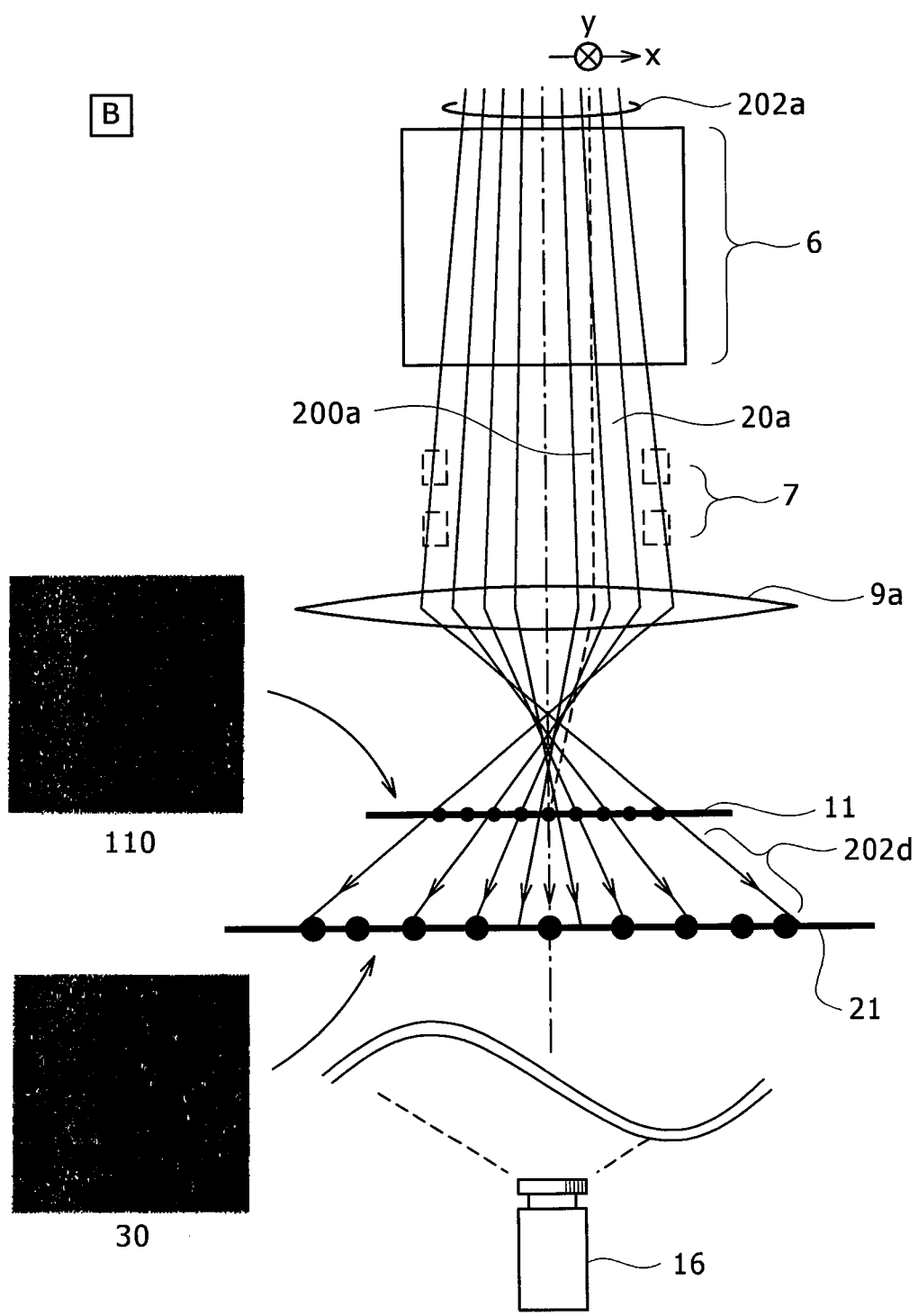
FIG. 5 shows the measurement principle of an aberration measuring method using a conventional Ronchigram.

FIG. 4 shows the outline of an electronic optical setting in the STEM for an aberration measuring method using a Ronchigram, as another conventional aberration measuring method. FIG. 5 is an enlarged view showing B of FIG. 4 to indicate the principle of the measuring method. A Ronchigram method does not use scanning electron microscope images obtained by the scanning coil 7 unlike the aberration measurement using displacement due to aberrations, the probe tableau method, and so on. As shown in FIG. 4, the sample 11 is irradiated with an incident electron beam 202a to obtain a Ronchigram 21 as a projected image for measurement. The Ronchigram 21 is properly projected on the surface of a scintillator or the like through the imaging lens 12 and is observed by an electron beam detector (an EELS detector or an imaging detector) 16 such as a camera. Since the sample 11 is irradiated with the large-angle beam, the incident electron beam 202a is focused properly near the sample 11 as shown in the enlarged view of FIG. 5. Thus, for example, points at regular intervals on the sample 11 are projected by electron beams including different aberrations at different incident angles, obtaining projected sample images that contain deviations or distortions with reflected aberrations. In other words, the distorted projection image 21 is a Ronchigram. It is known that the Ronchigram has a local distortion tensor (x, y) determined by (Equation 6) using the wave aberration $\chi(\omega, \omega^c)$ of (Equation 2).

[Expression 9]

$$\zeta(x, y) = \begin{pmatrix} \partial_{xx} \chi & \partial_{xy} \chi \\ \partial_{xy} \chi & \partial_{yy} \chi \end{pmatrix} \quad \text{(Equation 6)}$$

In this expression, $\chi(\omega, \omega^c)$ is expressed as $\chi$ for simplification. Moreover, x and y are coordinates on the Ronchigram for incident angle $\omega s = x+iy$. As in the above measuring method, a simultaneous equation in (Equation 6) can determine an aberration coefficient.

It should be noted that the above method needs to repeatedly obtain electron microscope images at multiple measurement points, whereas in the Ronchigram method, distortions at multiple points are measured by the single Ronchigram so as to form the simultaneous equation in (Equation 6), satisfactorily determining an aberration coefficient.

As an example of such an aberration measuring method using a Ronchigram, Patent Literature 3 describes a method of obtaining a transmission Ronchigram 30 using an amorphous thin-film sample 11. An autocorrelation is obtained in a local region of the transmission Ronchigram 30 to obtain a local distortion tensor of the Ronchigram. A proper region of the obtained transmission Ronchigram 30 is divided in a grid pattern, and an autocorrelation is calculated for each point. Thus, an oval autocorrelation pattern with a local distortion is obtained for each point.

[Expression 10]

$$(Au + Bv)^2 + (Bu + Cv)^2 = const. \quad \text{(Equation 7)}$$

$$\begin{cases} A \equiv \partial_{xx} \chi \\ B \equiv \partial_{xy} \chi \\ C \equiv \partial_{yy} \chi \end{cases}$$

This can derive aberration coefficients from the simultaneous equation of (Equation 6) based on the oval autocorrelation patterns. In this equation, (u, v) represents the local coordinates of a grid with respect to an origin point located at the center of the grid.

As described above, in the aberration measuring method using a Ronchigram, an aberration can be theoretically measured from a single Ronchigram. Actually, a plurality of Ronchigrams is more properly used to obtain conditions for normalizing the absolute magnitudes of aberration coefficients or reduce an error. Original data can be obtained for calculating aberration coefficients with a sufficiently small number of measurements as compared with the aberration measurement using displacement due to aberrations and the probe tableau method. Since a Ronchigram is a projected image, a measurement image is expected to be captured in a short time. Thus, an aberration can be measured at a high speed by using a Ronchigram. This method is quite promising in the adjustment of an aberration corrector requiring repeated aberration measurements.

In the case where an image containing the same aberration information as in a Ronchigram is obtained by an image formed by a scanning method, such an image can be obtained by, for example, the method of FIG. 6. The electron source 2, the converging lens 3, the aberration corrector 6, the objective lenses 9a and 9b, and an electron detector for a bright field detector and a dark field ring-shaped detector are provided as in the standard aberration correction STEM of FIG. 1. Similarly, the sample 11 is set on a standard position for a STEM observation with a sample holder 19. Optical elements for aberration measurements include the aberration corrector 6 contributing to the formation of a probe on the surface of the sample 11 and the front field 9a of the objective lens. Thus, in order to obtain a scan image, a probe is two-dimensionally scanned on the surface of the sample 11 by using a scanning coil 23 for a scanning Ronchigram attached on a measured lens, instead of the typical scanning coil 7. The scanning coil 23 for a scanning Ronchigram requires high dynamic responsivity for scanning a beam and thus is desirably separated from a deflection coil. However, the scanning coil 23 may be used with a deflection coil as long as responsivity can be sufficiently obtained by the electron beam deflector 5 used in the probe tableau method.

Furthermore, the diaphragm 4 for a scanning Ronchigram is provided above the scanning coil 23 for a scanning Ronchigram to minutely limit electron beams before scanning. With this configuration, the beam 203a is scanned on the measured lens (the aberration corrector 6 and the objective-lens front field 9a), allowing a distorted beam probe with a reflected aberration of the lens to scan the surface of the sample. A scattered electron beam 203d obtained from the beam probe is properly adjusted by the imaging lens 12 and the deflector 13 that are located below the electron beam, and is collected by the STEM bright field detector 15 or the STEM dark field ring-shaped detector 14. The electron beam is displayed as a scan image in synchronization with two-dimensional scanning in the scanning coil 23 for a scanning Ronchigram, obtaining a scan image containing distortion information with an aberration.

Figure 7:
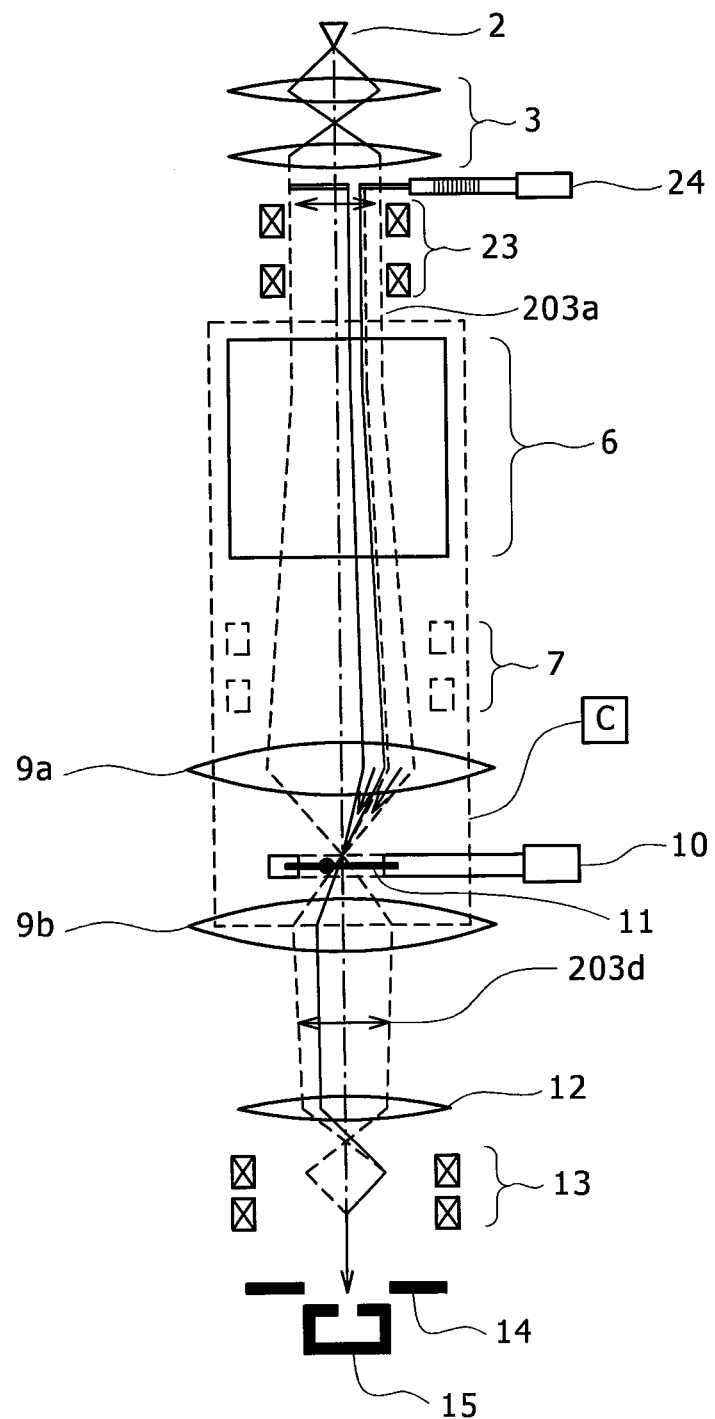
FIG. 7 shows another electronic optical setting of the scanning transmission electron microscope, the setting being made for performing the scanning Ronchigram method according to the present invention in the scanning transmission electron microscope.

As shown in FIG. 7, in similar beam scanning, a diaphragm 24 for measured lens information is provided with a scanning function driven by a piezo element or the like without using an electromagnetic scanning coil. Thus, a scan image obtained in synchronization with scanning of the diaphragm 24 can contain the same aberration information as in FIG. 6.

Figure 8:
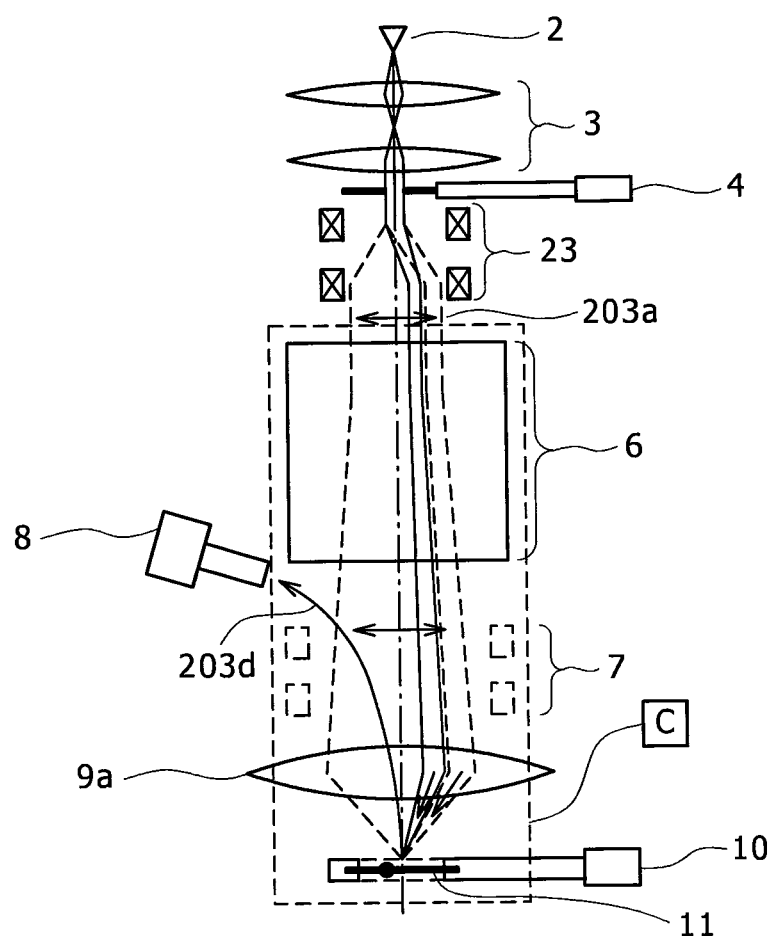
FIG. 8 shows still another electronic optical setting of the scanning transmission electron microscope, the setting being made for performing the scanning Ronchigram method according to the present invention in the scanning transmission electron microscope.

Since a scan image is obtained, it is not always necessary to obtain a transmission image. Thus, as shown in FIG. 8, a reflected/secondary electron beam generated by a scanning probe in FIGS. 6 and 7 is collected by a SEM detector to form a scan image synchronized with two-dimensional scanning on the measured lens, thereby obtaining a scan image with reflected aberration information also in SEM.

Figure 9:
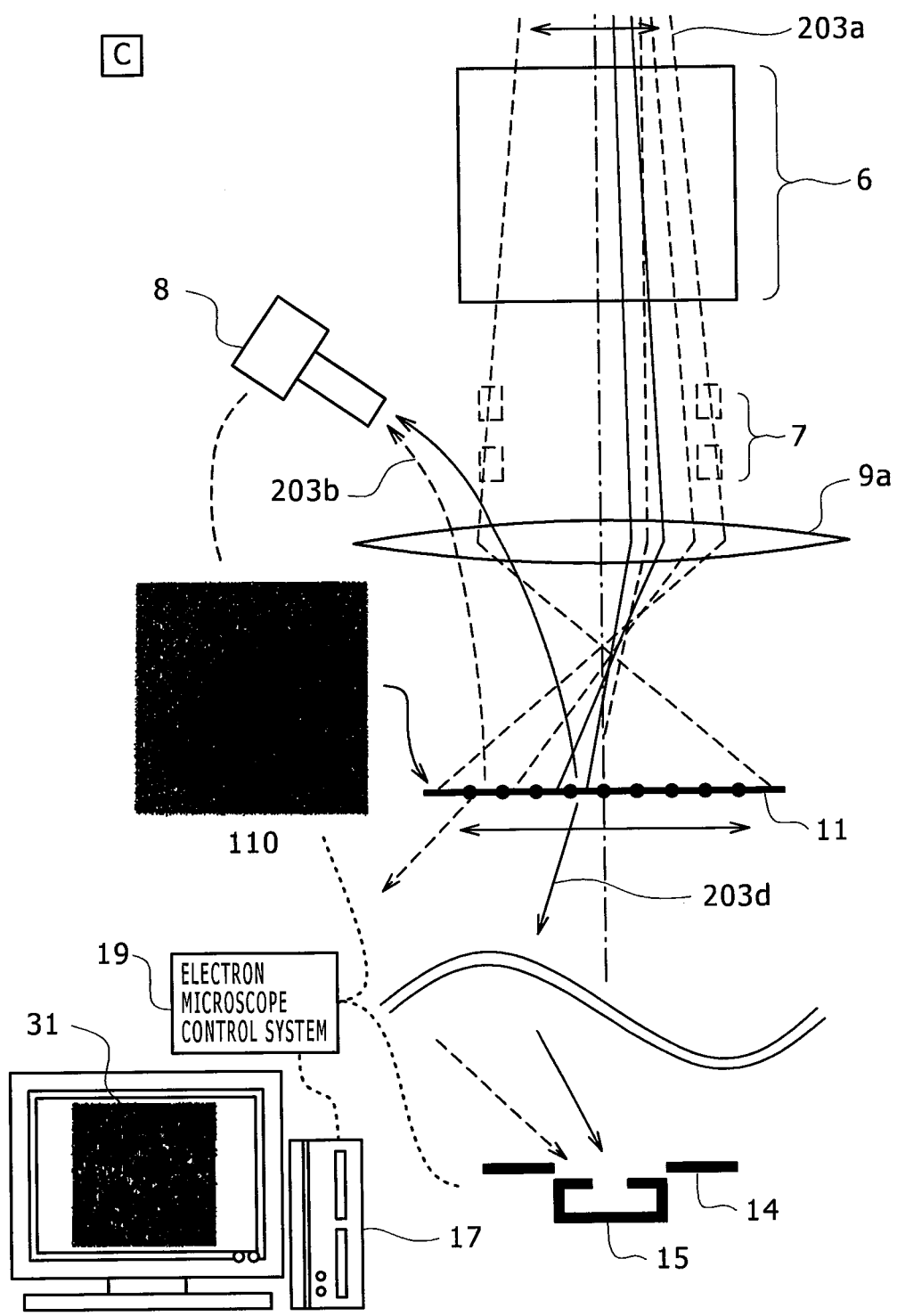
FIG. 9 shows the principle of the scanning Ronchigram method according to the present invention.

Referring to FIG. 9, the formation of an image similar to a Ronchigram (hereinafter, will be simply called "scanning Ronchigram") by the scanning method will be more specifically described below. The electron beam 203a focused by the above method is scanned above the aberration corrector 6 with an aberration to be measured and the objective-lens front field 9a, which corresponds to a change of an electron illumination angle with respect to the measured lenses. Thus, a beam probe on the surface of the sample 11 is scanned while being distorted with an aberration. For example, even if the incident beam 203a is scanned at a constant speed, a scanning probe on the surface of the sample moves with velocity modulation (and a distortion) with a reflected aberration. This state is similar to the divided and observed incident electron beam 202a for forming a Ronchigram, unlike in FIG. 5 illustrating the formation of a conventional transmission Ronchigram. A reflected/secondary electron beam generated from the sample 11 by the probe is detected by the SEM detector 8, or a scattered electron beam is detected by the STEM dark field detector or the bright field detector (14, 15), thereby displaying a scanning Ronchigram 31 on an electron microscope control console 17 through the electron microscope control system 19. If calculators such as a PC and a workstation are used on the electron microscope control console 17, a scanning Ronchigram can be recorded and analyzed while being displayed. An aberration coefficient can be derived at the same time.

The equivalence of the scanning Ronchigram 31 and the conventional transmission Ronchigram 21 is expressed by an equation below. In consideration of the formation of the transmission Ronchigram, a beam probe $p(x_s, y_s)$ on the surface of the sample 11 with a reflected aberration is expressed as a Fourier transform with a wave aberration of $\chi(\omega, \omega^c)$.

[Expression 11]

$$p(x_s, y_s) = F[\chi] \quad \text{(Equation 8)}$$

In this expression, $F[\ ]$ represents the Fourier transform and $\chi(\omega, \omega^c)$ is abbreviated as $\chi$ as in the above explanation. $(x_s, y_s)$ indicates coordinates on the surface of the sample. If the coordinates of the sample irradiated with the probe are $s(x_s, y_s)$, the transmission Ronchigram $\psi(\omega')$ 21 is expressed by an inverse Fourier transform $F^{-1}[\ ]$ of the probe $\rho(x_s, y_s)$ weighted by the sample.

[Expression 12]

$$\psi_T(\omega') = F^{-1}[p(x_s,y_s) \cdot s(x_s,y_s)] = F^{-1}[F[\chi] \cdot s(x_s,y_s)] \quad \text{(Equation 9)}$$

The scanning Ronchigram 31 may be Ronchigrams superimposed by the scanning Ronchigram diaphragm 24 for measured lens information, and thus the scanning Ronchigram 31 may be expressed by a convolution with a diaphragm transmission function $t(\omega')$ as follows:

[Expression 13]

$$\psi_s(\omega') = \psi_t(\omega') \otimes t(\omega') \quad \text{(Equation 10)}$$

[Expression 14]

$\otimes$ indicates a convolution.

Thus, a sufficiently small diaphragm diameter and $\delta$ functional $t(\omega')$ are expressed as follows:

[Expression 15]

$$\omega_s(\omega') \approx \psi_t(\omega') \quad \text{(Equation 11)}$$

The scanning Ronchigram 31 seems to be substantially equivalent to the transmission Ronchigram 21. In other words, an analysis method used for a transmission Ronchigram to measure an aberration is substantially applicable to an analysis on the scanning Ronchigram 31.

Figure 10:
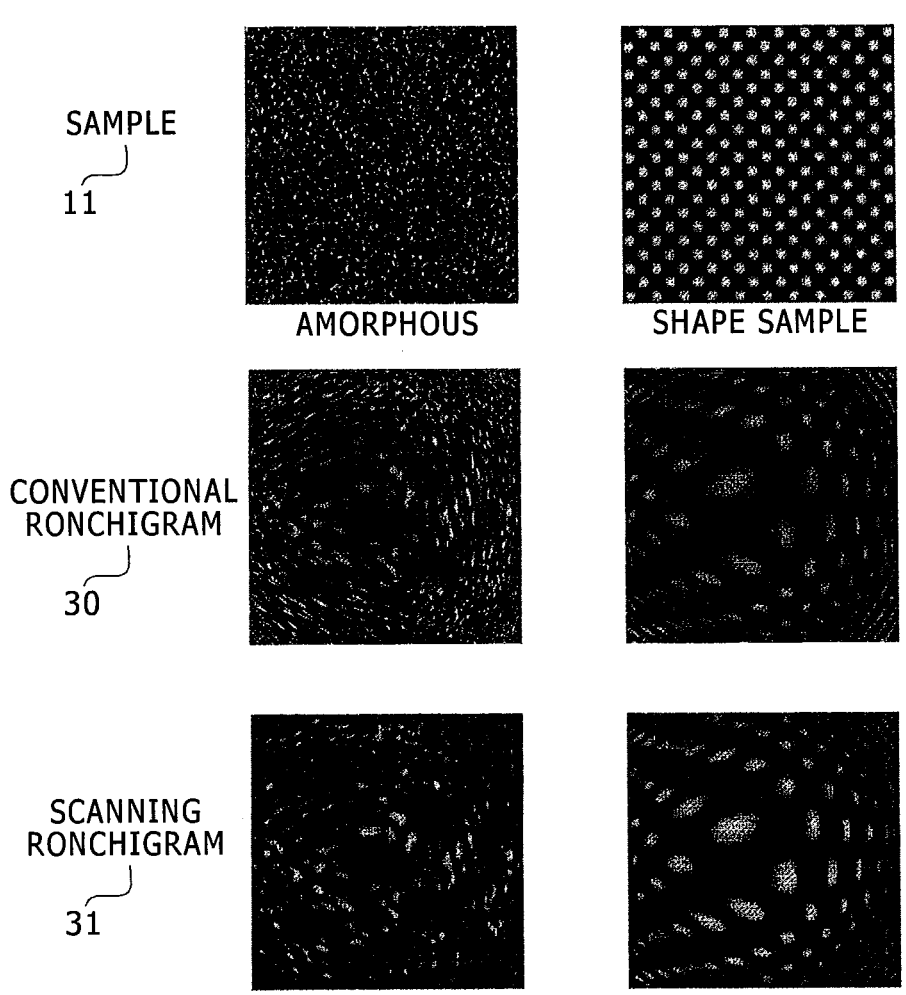
FIG. 10 shows a comparison between examples of a conventional Ronchigram image and a scanning Ronchigram image that are captured from an amorphous measurement sample and a shaped measurement sample.

Against this backdrop, FIG. 10 shows a comparison between the transmission Ronchigram (conventional method) 39 and the scanning Ronchigram 31 of the present invention. For example, in the case where the sample is an amorphous thin film 110, an obtained transmission Ronchigram and an obtained scanning Ronchigram have similar distortion patterns. Thus, a local distortion analysis as on the transmission Ronchigram can be conducted by the same analysis method as in Patent Literature 3 to derive an aberration coefficient. Also in the case of a clearly shaped sample as in SEM, an aberration coefficient can be derived by a distortion analysis on a similar Ronchigram. In the case of a sample having a characteristic shape point, a distortion of a scanning Ronchigram is evaluated by evaluating a displacement of a characteristic point with respect to a typical SEM image. An aberration coefficient can be derived using the distortion.

A feature of the scanning Ronchigram method in FIG. 9 is that multiple electron beams are collectively focused in a small region of the sample when an aberration is measured, unlike in the conventional transmission Ronchigram method in FIG. 5. In the conventional transmission Ronchigram method, as shown in FIG. 5, multiple electron beams needs to be focused near the surface of the sample. This accelerates contamination of the sample and causes heat from the electron beams to locally deform the thin film of the sample, which may cause a measurement error.

According to the scanning Ronchigram method of the present invention, electron beams have been reduced to a minimum dose by the converging lens diaphragm 4 and then the surface of the sample is scanned. This is unlikely to accelerate contamination on the sample or local deformation on the thin film of the sample. Therefore, according to the scanning Ronchigram method of the present invention, the Ronchigram pattern 31 is more stably obtained than in the conventional transmission Ronchigram method. Thus, an aberration is expected to be measured with higher accuracy.

Figure 11:
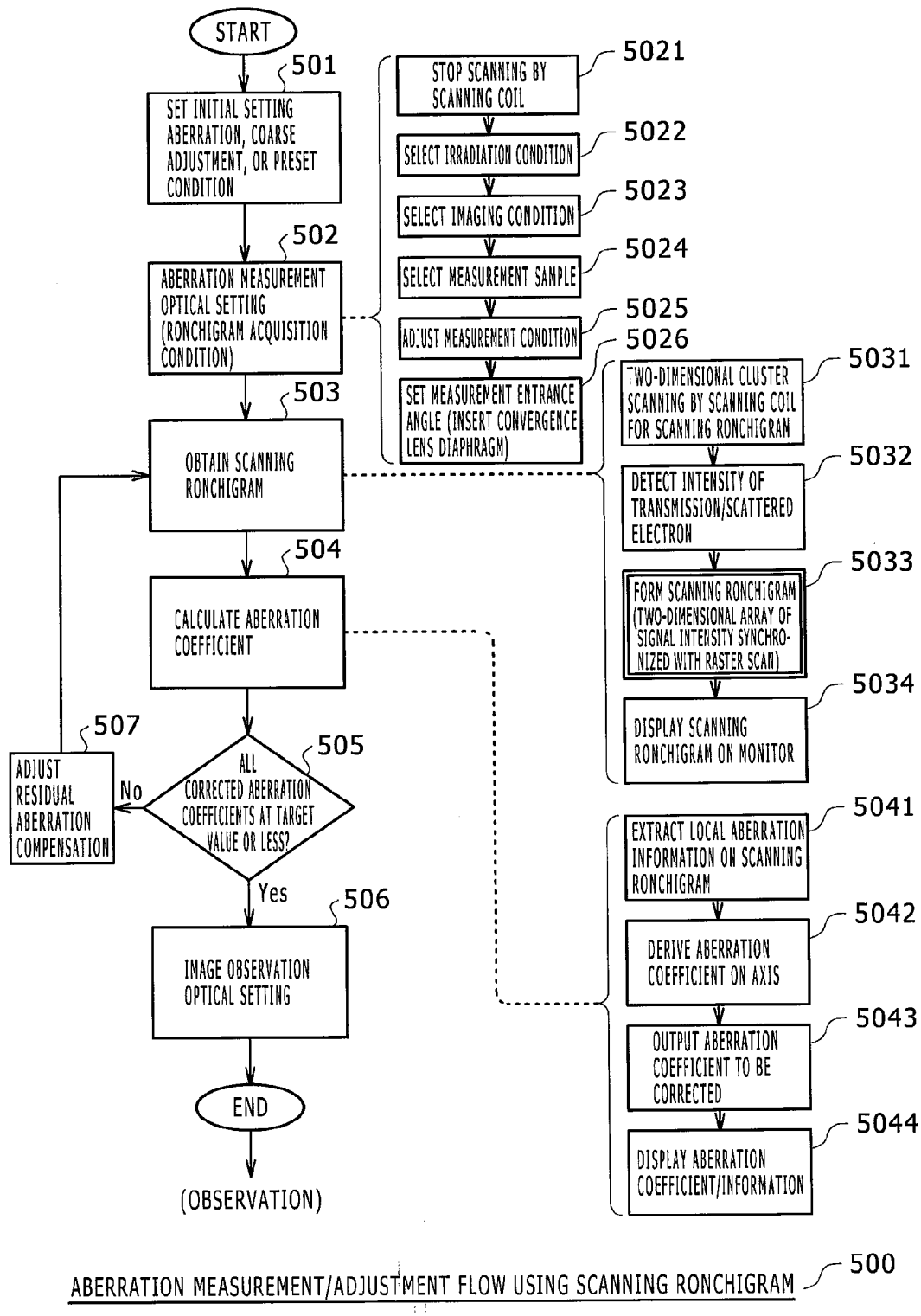
FIG. 11 is a flowchart showing an example of an aberration measurement and an aberration adjustment in the use of the scanning Ronchigram method according to the present invention.

FIG. 11 shows a work flow example 500 for measuring an aberration and adjusting an aberration corrector. First, an initial setting 501 is made for an electron microscope to obtain a state close to desired conditions for correcting aberrations. Thus, after a coarse adjustment on a device, it is expected to routinely restore a reading state of proper preset values prepared for a lens in an electron microscope, a deflector, and an aberration corrector. Subsequently, Ronchigram measurement conditions 502 are set to perform close control using aberration measurements according to the scanning Ronchigram method.

As shown in FIGS. 6 to 9, in order to obtain a typical scanning microscope image, scanning is stopped 5021 by the scanning coil is performed, irradiation conditions are adjusted 5022 by the converging lens to obtain proper contrast and brightness under Ronchigram observation conditions, and then the imaging lens is adjusted 5023 so as to obtain a projected image at a proper magnification. At this point, the same conditions as in a proper observation of the conventional Ronchigram.

Furthermore, a measurement sample is selected 5024 for a sample portion suitable for measurement by, for example, a sample fine adjustment ordinarily provided in the electron microscope, and then measurement conditions such as defocus and a projection magnification are adjusted 5025. The measurement conditions vary depending upon aberration analysis methods from a Ronchigram, which will be described later. Proper conditions are determined for the respective methods. The converging lens diaphragm 4 is selected and inserted to limit 5026 the entrance angle of an electron beam to obtain a scanning Ronchigram. For example, in the case of a 200-kv aberration correction STEM, it is suitable to use a diaphragm having a convergent angle of 5 to 10 mrad on the surface of the sample.

Subsequently, a scanning Ronchigram is obtained using the setting. While the ordinary scanning coil 7 is stopped, two-dimensional raster scanning 5031 is performed using the scanning coil 23 for a scanning Ronchigram, upstream of an aberration corrector and an aplanatic measurement lens such as an objective lens. The intensity of a transmission scattered electron, a reflected electron, and a secondary electron is measured 5032 through a detector and is converted 5033 to a two-dimensional intensity distribution synchronized with raster scan. The intensity distribution (image) obtained thus is optionally displayed 5034 on a monitor or the like by a scanning Ronchigram.

Moreover, an aberration is measured, in other words, an aberration coefficient is calculated 504 by using an aberration analysis method compliant with an analysis method from the conventional transmission Ronchigram. For this calculation, an image shift, defocus, an astigmatic amount, and local aberration information on a scanning Ronchigram associated with the astigmatic amount are extract 5041 on each portion of the scanning Ronchigram, and then an aberration coefficient (on the axis) is derived 5042 by the same analysis method used for the conventional transmission Ronchigram method analysis. This result is outputted 5043 to an aberration adjustment program as an aberration coefficient to be corrected, and aberration coefficient/information is optionally displayed 5044 as an aberration coefficient and a wave aberration pattern on a monitor.

An aberration correction state is decided 505 based on the measured aberration coefficient. In the case where a residual aberration is larger than a desired value, residual aberration compensation is adjusted 507 for the aberration corrector, the lenses, e.g., the objective lens in the electron microscope, and the electron optical device, e.g., the deflector so as to reduce the aberration. It is decided whether the adjustment is sufficient or not as follows: a scanning Ronchigram is obtained 503 again, an aberration coefficient is calculated 504, and then an aberration state is decided 505 depending upon whether an aberration to be reduced is sufficiently small or whether another aberration has increased in a derived manner. Typically, such a measurement and an adjustment loop are repeated several times, so that all the aberration coefficients to be adjusted are reduced to a desired value or less so as to complete an aberration adjustment. The aberration measurement setting is switched to a microscope image observation optical setting 506, shifting to an observation of an electron microscope image.

Figure 12:
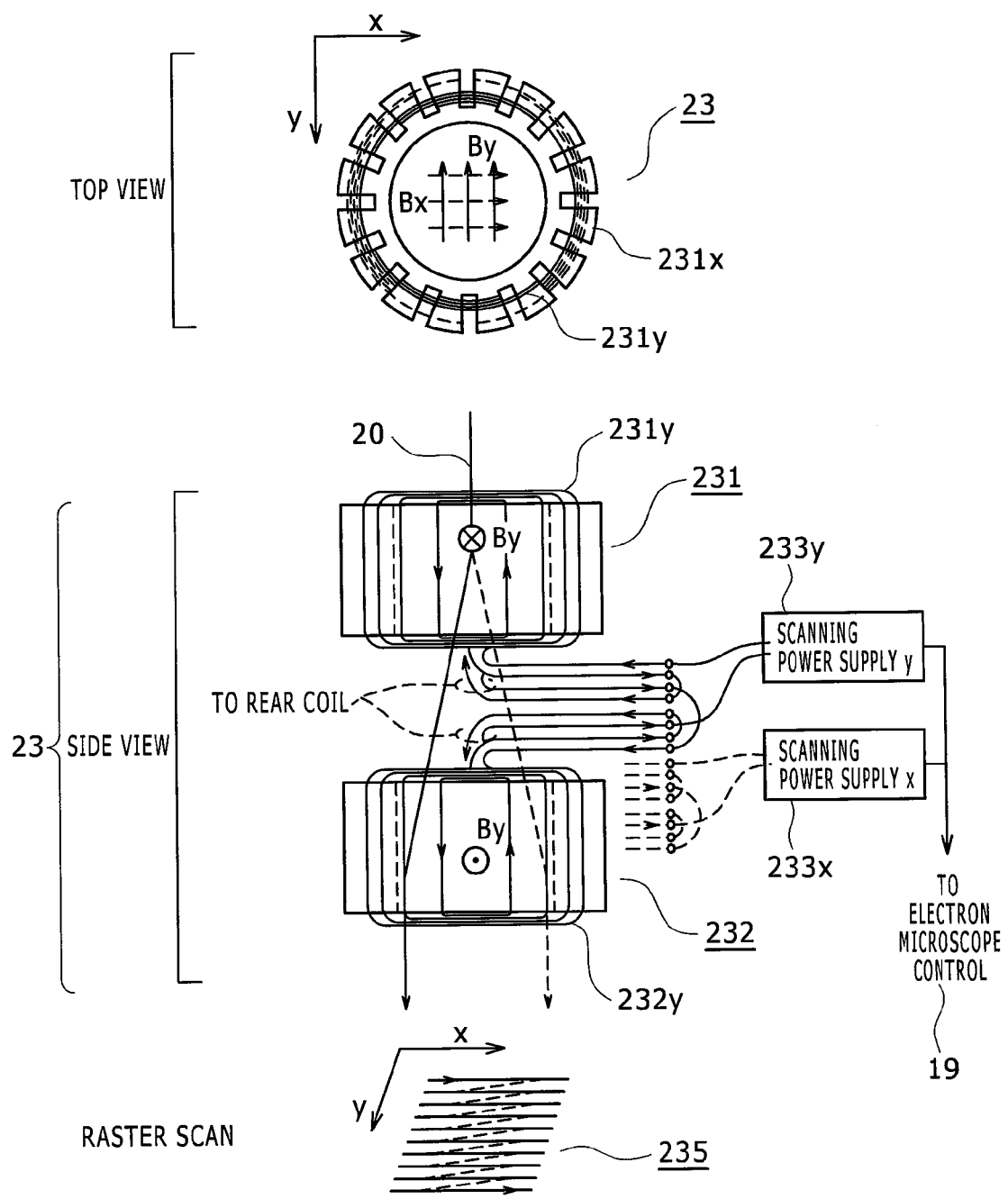
FIG. 12 shows a structural example of a scanning coil that is suitable for the scanning Ronchigram method of the present invention and is disposed upstream of an aplanatic measurement lens.

FIG. 12 shows an example of the scanning coil 23 used for obtaining a scanning Ronchigram. In the case where the scanning coil 23 is used in the aberration correction electron microscope, accurate two-dimensional raster scan 235 of an electron beam 2e requires a uniform deflected field in x and y directions around the central axis of the deflector and requires accurate electron beam shift scan that involves no excessive angular variations in two upper and lower coils so as to obtain vertical incidence on the top surface of a corrector. In an example of a 200-kV STEM, a uniform deflected field is desirably obtained approximately in the range of 500×500 µm$^2$ with respect to a deflection coil axis and an electron beam shift desirably keeps a parallelism of $5\times10^{-6}$ rad or less. Thus, for exciting coils 231 and 232 in FIG. 12, so-called "cosine windings" 231x and 231y and 232x and 232y are used in x and y directions so as to widely produce a uniform deflected field. Furthermore, the two vertically symmetrical coils 231 and 232 are used to obtain a high parallelism for an electron beam shift. (In the side view of FIG. 23, the coil windings in the x direction are omitted and only the coil windings 231y and 232y in the y direction are illustrated to avoid complexity. Actually, as shown in the top view, the coils 231x and 232x (not shown) are wound in the x direction orthogonal to 231y and 232y.)

An electron beam is scanned above the measured lens by using the foregoing devices and means, achieving a scanning Ronchigram equivalent to the conventional transmission Ronchigram without repeating complicated measurements while changing an electron illumination angle as in the probe tableau method. Furthermore, an aberration can be measured by the same analysis means as a transmission Ronchigram. Unlike in the conventional Ronchigram method, as shown in FIGS. 6 and 8, this method is applicable to a SEM that cannot use a transmission scattered electron beam of the sample. Moreover, an existing bright field, an existing dark field, an existing secondary electron detector, and so on can be used in a STEM. Hence, an imaging camera required for observing the conventional transmission Ronchigram is not always necessary in the method of the present invention, which is a feature of the aberration measuring method using "scanning Ronchigram method" according to the present invention.

REFERENCE SIGNS LIST 1 scanning transmission electron microscope body containing a spherical aberration corrector
2 electron source
3 converging lenses
4 converging lens diaphragm
5 electron beam deflector
6 aberration corrector
7 scanning coil (electron beam deflector)
8 SEM secondary electron/reflected electron detector
9 objective lens
9a objective lens front field
9b objective lens rear field
10 sample holder
11 observed/measured sample
11o observed/measured sample (over-focus position)
11u observed/measured sample (under-focus position)
100 scanning transmission electron microscope (STEM)
110 amorphous thin film (measured sample)
12 imaging lenses
13 electron beam deflector
14 STEM dark field detector (large-angle scattered electron ring-shaped detector)
15 STEM bright field detector (small-angle scattered electron detector)
16 electron beam detector (EELS detector or an imaging detector)
17 electron microscope control console
18 aberration corrector control system and power supply
19 electron microscope control system and power supply
202a incident electron beam
20 electron beam
20b reflected electron beam (or secondary electron beam)
20c transmitted electron beam
20d scattered electron beam
200a incident electron beam orbit without an aberration
201x incident electron beam x orbit with an aberration
201y incident electron beam y orbit with an aberration
203a incident electron beam for obtaining a scanning Ronchigram
203b reflected/secondary electron beam for obtaining a scanning Ronchigram
203d transmitted/scattered electron beam for obtaining a scanning Ronchigram
21 distorted projection image
23 scanning coil for a scanning Ronchigram (electron beam deflector)
231 upper deflection coil assembly of scanning coils for a scanning Ronchigram
231x coil winding for applying a deflected field in x direction as an upper coil
231y coil winding for applying a deflected field in y direction as an upper coil
232 lower deflection coil assembly of scanning coils for a scanning Ronchigram
231x coil winding (not shown) for applying a deflected field in x direction as a lower coil
231y coil winding for applying a deflected field in y direction as a lower coil
233x current source for driving the x-direction deflected field coils serving as upper and lower coils
233y current source for driving the y-direction deflected field coils serving as upper and lower coils
235 raster scan
24 diaphragm for a scanning Ronchigram
30 transmission Ronchigram
31 scanning Ronchigram
500 aberration measurement/adjustment flow using a scanning Ronchigram
501 initial setting (initial adjustment or preset condition setting)
502 aberration measurement optical condition setting
5021 stop of scanning by a scanning coil
5022 irradiation condition selection
5023 imaging condition selection
5024 measurement sample selection
5025 measurement condition adjustment
5026 measurement entrance angle setting
503 scanning Ronchigram acquisition
5031 two-dimensional raster scanning by a scanning coil for a scanning Ronchigram
5032 detection of transmission scattered electron intensity
5033 scanning Ronchigram formation (two-dimensional intensity distribution synchronized with raster scan)
5034 monitor display of a scanning Ronchigram
504 aberration coefficient calculation
5041 extraction of local aberration information on a scanning Ronchigram
5042 derivation of an aberration coefficient on an axis
5043 output of an aberration coefficient to be corrected
5044 monitor display of aberration coefficient/information
505 decision of an aberration correction state
506 switching to a microscope image observation optical setting
507 residual aberration compensation adjustment

The invention claimed is:
1. A method for measuring a lens aberration in a charged particle optical device including an electron source that emits an electron beam, sample mounting means for mounting a sample, electromagnetic lenses disposed between the electron source and the sample mounting means, electron beam scanning means that is disposed on an electron-optical upstream side of an aberration corrector and measured lenses of the electromagnetic lenses for scanning and deflecting the electron beam, detecting means, except for a projection-type detector, that detects an electron signal induced from the sample by the electron beam impinging onto the sample, and control means that controls the electron source, the electromagnetic lenses, the electron beam scanning means, and the detecting means, the method comprising the steps of:

two-dimensional scanning, by the electron beam scanning means upstream of the aberration corrector and the measured lenses, the electron beam from the electron source so as to scan a beam probe on a surface of the sample, the beam probe being formed by the electromagnetic lenses;

detecting, by the detecting means, at least one of signals including a secondary electron, a reflected electron, a transmitted electron, and a scattered electron that are induced by the beam probe projected with a distortion on the surface of the sample according to an aberration of the measured lenses; and calculating, by the control means, an aberration amount of the measured lenses based on a two-dimensional image of a scanned Ronchigram obtained in synchronization with the two-dimensional scanning by the electron beam scanning means upstream of the aberration corrector and the measured lenses.

2. The method for measuring a lens aberration according to claim 1, wherein the charged particle optical device is a scanning transmission electron microscope.

3. The method for measuring a lens aberration according to claim 1, wherein the charged particle optical device is a scanning electron microscope.

4. The method for measuring a lens aberration according to claim 1, wherein the control means sets optical conditions for lens aberration measurement according to the steps of:
a) setting an initial condition for controlling the electromagnetic lenses and the electron beam scanning means;
b) setting aberration measurement optical conditions for obtaining a Ronchigram;
c) obtaining a scanning Ronchigram while irradiating the sample with the scanned electron beam based on the aberration measurement optical conditions;
d) calculating an aberration coefficient based on the obtained scanning Ronchigram;
e) deciding whether the calculated aberration coefficient is equal to or smaller than a target value, and
f) setting optical conditions for lens aberration measurement when the calculated aberration coefficient is equal to or smaller than a target value.

5. A charged particle optical device comprising:
an electron source that emits an electron beam;
sample mounting means for mounting a sample;
electromagnetic lenses disposed between the electron source and the sample mounting means;
electron beam scanning means that is disposed on an electron-optical upstream side of an aberration corrector and measured lenses of the electromagnetic lenses, and scans and deflects the electron beam; and
control means that controls the electron source, the electromagnetic lenses, and the electron beam scanning means,
wherein the electron beam scanning means upstream of the aberration corrector and the measured lenses two-dimensionally scans the electron beam from the electron source so as to scan a beam probe on a surface of the sample, the beam probe being formed by the electromagnetic lenses, and
wherein the charged particle optical device further comprises:
detecting means that detects at least one of signals including a secondary electron, a reflected electron, a transmitted electron, and a scattered electron that are induced by the beam probe projected with a distortion on the surface of the sample according to an aberration of the measured lenses; and
measuring means that measures an aberration amount of the measured lenses based on a two-dimensional image of a scanned Ronchigram obtained in synchronization with the two-dimensionally scanning by the electron beam scanning means upstream of the aberration corrector and the measured lenses,
wherein the detecting means does not include a projection-type detector.

6. The charged particle optical device according to claim 5, wherein the measured lenses include: an objective lens front field that is disposed upstream of the sample and focuses the electron beam on the surface of the sample, and
an aberration corrector disposed between the objective lens front field and the electron beam scanning means.

7. The charged particle optical device according to claim 5, wherein the charged particle optical device is a scanning transmission electron microscope,
the charged particle optical device further including a beam aperture system that focuses a beam shape scanned by the electron beam scanning means into a predetermined beam diameter, upstream of the electron beam scanning means.

8. The charged particle optical device according to claim 5, wherein the charged particle optical device is a scanning electron microscope,
the charged particle optical device further including a beam aperture system that focuses a beam shape scanned by the electron beam scanning means into a predetermined beam diameter, upstream of the electron beam scanning means.

9. The charged particle optical device according to claim 5, further comprising:
a beam aperture system that focuses a beam shape scanned by the electron beam scanning means into a predetermined beam diameter, upstream of the electron beam scanning means,
wherein the electron beam having the predetermined beam diameter is mechanically scanned by amplitude-shifting the beam aperture system without scanning the electron beam by means of the electron beam scanning means.

* * * * *